United States Patent [19]

Bernáth et al.

[11] Patent Number: 4,656,179
[45] Date of Patent: Apr. 7, 1987

[54] ISOQUINOLINE DERIVATIVES, AND PHARMACEUTICAL COMPOSITIONS CONTAINING THEM

[75] Inventors: Gabor Bernáth; Jenö Kòbor; Ferenc Fülöp, all of Szeged; Elemér Ezer, Budapest; Gyorgy Hajós, Budapest; Eva Palosi, Budapest; László Denes, Budapest; László Szporny, Budapest, all of Hungary

[73] Assignee: Richter Gedeon Vegyeszeti Gyar R.T., Budapest, Hungary

[21] Appl. No.: 664,842

[22] Filed: Oct. 25, 1984

[30] Foreign Application Priority Data

Oct. 25, 1983 [HU] Hungary ............... 3651/83

[51] Int. Cl.⁴ ................ A61K 31/47; C07D 217/16
[52] U.S. Cl. .................................. 514/307; 546/150
[58] Field of Search .................. 546/150; 514/307

[56] References Cited

FOREIGN PATENT DOCUMENTS

EP-143333  6/1985  European Pat. Off. ............ 546/150

Primary Examiner—Glennon H. Hollrah
Assistant Examiner—James H. Turnipseed
Attorney, Agent, or Firm—Keil & Weinkauf

[57] ABSTRACT

The invention relates to new 1-[bis(hydroxymethyl)-methyl]-3,4-dihydro- or -1,2,3,4-tetrahydroisoquinoline derivatives of the formula (I)

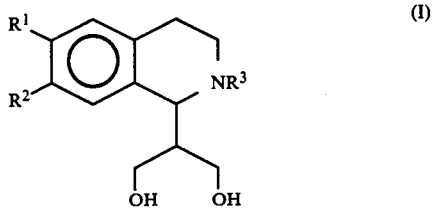

wherein
$R^1$ and $R^2$ represent hydroxyl or alkoxy having from 1 to 6 carbon atoms,
$R^3$ is hydrogen or a single electron pair,
and the dotted line represents an optional double bond, and salts thereof.

The new compounds are useful intermediates in the preparation of other, pharmaceutically active isoquinoline derivatives or are pharmaceutically active themselves.

3 Claims, No Drawings

ISOQUINOLINE DERIVATIVES, AND PHARMACEUTICAL COMPOSITIONS CONTAINING THEM

The invention relates to new isoquinoline derivatives. More particularly, the invention concerns new 1-[bis(-hydroxymethyl)-methyl]-3,4-dihydro- or -1,2,3,4-tetrahydroisoquinoline derivatives of the formula (I)

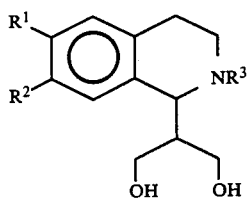

wherein
$R^1$ and $R^2$ each may stand for hydroxyl or alkoxy having from one to 6 carbon atoms,
$R^3$ is hydrogen or a single electron pair,
and the dotted line represents an optional double bond,
and salts thereof.

According to another aspect of the invention there is provided a process for the preparation of the compounds of formula (I), wherein $R^1$, $R^2$, $R^3$ and the dotted line have the same meanings as defined above, and salts thereof, which process comprises reacting a 1-methyl-3,4-dihydroisoquinoline derivative of the formula (II)

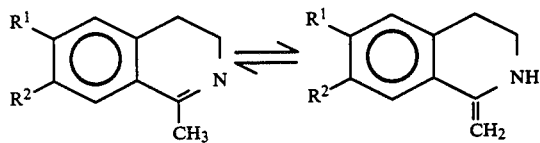

or a 1-(β-hydroxyethyl)-3,4-dihydroisoquinoline derivative of the formula (III)

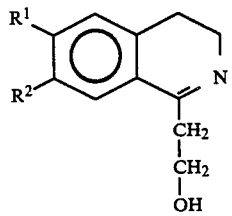

wherein $R^1$ and $R^2$ are as defined above, with formaldehyde, or the hydrate or trimeric derivative thereof. The reaction is preferably carried out in an alkaline medium. The corresponding 1,2,3,4-tetrahydro-derivatives may then be prepared by hydrogenation of the 3,4-dihydro-compounds obtained.

If desired, in the compounds of the formula (I) $R^1$ and/or $R^2$ may be converted into another group within the definition of $R^1$ and $R^2$ and, if desired, compounds of the formula (I) can be converted into the salts thereof.

The compounds of the formula (I) are useful intermediates in the preparation of pharmaceutically active isoquinoline derivatives. Thus, they can be converted into various pharmaceutically active N-substituted bis(-hydroxymethyl)-methyl-isoquinoline derivatives having for example immunsuppressive, anticonvulsive, analgesic or antipyretic activity, by conventional techniques of N-substitution. Further details of this process are disclosed in Hungarian patent application No. 3652/83 which corresponds to our copending and allowed U.S. application Ser. No. 664,770 filed Oct. 25, 1984. Further valuable compounds are obtained if in the compounds of the formula (I) one or both hydroxyls of the bis(hydroxymethyl)-methylene group are replaced by other substituents, e.g. acyl groups. Substitution is carried out by conventional reactions which are disclosed in our co-pending Hungarian patent application No. 3653/83. The compounds obtained are biologically active, thus possess immunsuppressive, antidepressive, analgesic, antipyretic, antihipoxial or gastric acid secretion inhibiting activity.

Certain representatives of the compounds of formula (I) are pharmaceutically active themselves, e.g. show neuroleptic and anticonvulsive activity. Therefore, according to a still further aspect of the invention there are provided pharmaceutical compositions containing compounds of the formula (I) or pharmaceutically acceptable salts thereof, in admixture with conventional pharmaceutical carriers and/or diluents.

According to Chem. Ber. 102, 915 (1969) 1-[bis(hydroxymethyl)-methyl]-isoquinoline was prepared from 1-methylisoquinoline with formaldehyde. The compound was obtained in a yield of 60%, after boiling for 40 hours. The authors examined only one chemical reaction of the compound obtained: its hydrogenation in the presence of a platinum oxide catalyst, which afforded the corresponding 5,6,7,8-tetrahydro-isoquinoline in a 30% yield. It was neither disclosed nor suggested that the compounds could be converted into other, pharmaceutically active derivatives or might be pharmaceutically active themselves.

In the above formulae $R^1$ and $R^2$ as an alkoxy having from 1 to 6 carbon atoms represent straight or branched chained alkoxy groups having from 1 to 6 carbon atoms, such as methoxy, ethoxy, n- or isopropoxy, n-, sec- or tert-butoxy, n- or isopentoxy, n- or isohexyloxy groups; preferably alkoxy groups having from 1 to 4 carbon atoms; most preferably methoxy or ethoxy.

The 1-methyl- and 1-(β-hydroxyethyl)-isoquinoline derivatives of the formulae (II) and (III) used as starting materials, in which $R^1$ and $R^2$ are as defined above, are known in the art, and can for example be prepared from homoveratryl amine or the corresponding β-phenylethyl amine derivative by acetylation and a subsequent ring closure conventionally used for preparing isoquinoline compounds, e.g. Bischler-Napieralski synthesis.

As a partner in the reaction formaldehyde, the hydrate or trimeric derivative thereof, i.e. paraformaldehyde or trioxane, is used, which are commercially available materials.

The reaction is preferably carried out in alkaline medium, most preferably in the presence of an alkali metal alcoholate or alkali metal hydroxide. As an alkali metal alcoholate for example sodium methylate or sodium ethylate, as an alkali metal hydroxide for example sodium or potassium hydroxide is employed.

The starting compounds of the formulae (II) and (III) are preferably reacted with formaldehyde and derivatives thereof in an inert organic solvent, such as an alcohol having from 1 to 6 carbon atoms, e.g. methanol; or in an aromatic hydrocarbon, e.g. benzene.

Formaldehyde and derivatives thereof may be used in an equimolar amount related to the starting compounds, or in a slight excess. When starting from a 1-methyl-isoquinoline derivative of the formula (II) and using an equivalent amount or slight excess of formaldehyde, a small amount of a 1-(β-hydroxyethyl)-isoquinoline derivative can also be isolated as a by-product, which can easily be separated from the main product, e.g. by recrystallization from ether.

The reaction temperature may be varied within wide limits, but preferably it is between room temperature and the reflux temperature. Most preferably the reaction is carried out around room temperature. The reaction time is a function of temperature and other reaction conditions, e.g. the reactants and medium employed, and generally amounts to several hours.

Hydrogenation can be performed with any conventional hydrogenating agent, such as a complex metal hydride or with hydrogen, in the presence of a catalyst. As a complex metal hydride for example sodium-tetrahydroborate (III) or lithium-aluminium hydride is employed. Catalytic hydrogenation is carried out under normal conditions, preferably in ethanol, in the presence of a catalyst conventionally used for hydrogenation, e.g. palladium-on-charcoal or platinum oxide.

Compounds of the formula (I) can be converted into the corresponding acid addition salts by reacting with acids.

Salt formation can be carried out in an inert organic solvent, for example in a $C_{1-6}$ aliphatic alcohol, by dissolving the compound of the formula (I) in the solvent and the selected acid or by adding a solution thereof formed with the same solvent to the first solution until it becomes slightly acidic (pH 5 to 6). Thereafter the acid addition salt separates out and may be removed from the reaction mixture e.g. by filtration.

The compounds of the formula (I) or the salts thereof, if desired, can be subjected to further purification, e.g. recrystallization. The solvents used for recrystallization are selected depending on the solubility and crystallization properties of the compound to be crystallized.

As mentioned before, in the compounds of the formula (I) the substituents $R^1$ and/or $R^2$ can easily be converted into other substituents within the definition of $R^1$ and $R^2$. For example compounds of the formula (I) in which $R^1$ and/or $R^2$ is hydroxyl can be converted into the corresponding compounds of the formula (I), in which $R^1$ and/or $R^2$ represent an alkoxy group having from 1 to 6 carbon atoms, by methods known in the art. The 6,7-dimethoxy compounds are most expediently prepared by methylation of the corresponding 6,7-dihydroxy compounds with diazomethane or dimethyl sulfate. The higher ethers can for example be prepared by the Williamson synthesis, using alkyl iodides. On the other hand, from compounds of the formula (I), in which $R^1$ and/or $R^2$ represent an alkoxy group having from 1 to 6 carbon atoms, the corresponding compounds containing hydroxyl as $R^1$ and/or $R^2$ can be obtained by known reactions, e.g. heating with hydrogen iodide or by means of anhydrous aluminium chloride.

The invention is elucidated in detail by the aid of the following non-limiting Examples.

EXAMPLE 1

Preparation of 1-[bis(hydroxymethyl)-methyl]-6,7-dimethoxy-3,4-dihydroisoquinoline To a suspension of 2.5 moles of paraformaldehyde in 300 ml of methanol 1 mole (205.3 g) of 1-methyl-6,7-dimethoxy-3,4-dihydroisoquinoline and subsequently freshly prepared sodium ethylate (1 g of sodium+50 ml of ethanol) are added at room temperature, with stirring. The reaction mixture is stirred for 5 to 6 hours, whereupon it is kept at 40° to 50 C.° for half an hour. The mixture is evaporated under reduced pressure and the obtained crystalline material is recrystallized from a mixture of acetone and ether. The aimed compound is obtained with a melting point of 129° to 131 C.°

Yield: 90%.

Analysis for $C_{14}H_{19}NO_4$ (265.31): calculated: C 63.38%, H 7.22%, N 5.28%; found: C 63.48%, H 7.67%, N 5.17%.

EXAMPLE 2

Preparation of 1-[bis(hydroxymethyl)-methyl]-6,7-diethoxy-3,4-dihydroisoquinoline The procedure described in Example 1 is followed except that instead of 1-methyl-6,7-dimethoxy-3,4-dihydroisoquinoline an equivalent amount of 1-methyl-6,7-diethoxy-3,4-dihydroisoquinoline is used as a starting material. Evaporation of the reaction mixture under reduced pressure and recrystallization of the crude product obtained from benzene yields the aimed compound.

Melting point: 112° to 114 C.°

Yield: 82%.

Analysis for $C_{16}H_{23}NO_4$ (293.36): calculated: C 65.51%, H 7.90%, N 4.77%; found: C 65.72%, H 8.27%, N 4.48%.

EXAMPLE 3

Preparation of 1-[bis(hydroxymethyl)-methyl]-6,7-dimethoxy-3,4-dihydroisoquinoline Following the procedure described in Example 1 but replacing sodium ethylate by an equivalent amount of sodium methylate as a catalyst, the aimed compound is obtained, which has the same melting point as given in Example 1.

Yield: 90%.

EXAMPLE 4

Preparation of 1-[bis(hydroxymethyl)-methyl]-6,7-dimethoxy-3,4-dihydroisoquinoline Following the procedure described in Example 1 but replacing sodium ethylate by an equivalent amount of sodium hydroxide as a catalyst, the aimed compound is obtained which has the same melting point as the product obtained in Example 1.

Yield: 73%.

EXAMPLE 5

Preparation of
1-[bis(hydroxymethyl)-methyl]-6,7-dimethoxy-3,4-dihydroisoquinoline To a solution of 2.5 moles of paraformaldehyde in 500 ml. of benzene 1 mole (205.3 g) of 1-methyl-6,7-dimethoxy-3,4-dihydroisoquinoline and subsequently freshly prepared sodium ethylate (1 g sodium+50 ml ethanol) are added at room temperature, with stirring. The reaction mixture is refluxed for 4 hours. The mixture is then evaporated under reduced pressure, and the obtained crystalline material is recrystallized from a mixture of acetone and ether. The aimed compound is obtained which has the same melting point as the product prepared in Example 1.

Yield: 70%.

EXAMPLE 6

Preparation of
1-[bis(hydroxymethyl)-methyl]-6,7-dimethoxy-3,4-dihydroisoquinoline To 1 mole (205.3 g) of 1-methyl-6,7-dimethoxy-3,4-dihydroisoquinoline 100 ml of a 30% aqueous formaldehyde solution and then freshly prepared sodium methylate (1 g of sodium+50 ml of methanol) are added. The mixture is then slightly refluxed in 500 ml of methanol for 2 hours. The reaction mixture is evaporated under reduced pressure and the obtained crystalline product is recrystallized from a mixture of acetone and ether. The aimed compound is obtained with the same melting point as the product of Example 1.

Yield: 79%.

EXAMPLE 7

Preparation of
1-[bis(hydroxymethyl)-methyl]-6,7-dimethoxy-3,4-dihydroisoquinoline Following the procedure described in Example 1 but replacing paraformaldehyde by an equivalent amount of trioxane, the aimed compound is obtained with the same melting point as the product of Example 1.

Yield: 86%.

EXAMPLE 8

Preparation of the acid addition salts of dihydrocompounds 0.1 mole of 1-[bis(hydroxymethyl)-methyl]-6,7-dimethoxy-3,4-dihydroisoquinoline obtained in Example 1 is dissolved in 180 ml of absolute ethanol, and then a 1.5-fold excess of dry hydrogen chloride gas dissolved in absolute ethanol is added to the solution. After recrystallization from a mixture of methanol and ether the obtained 1-[bis(hydroxymethyl)-methyl]-6,7-dimethoxy-3,4-dihydroisoquinoline hydrochloride melts at 181° to 184 C.°

Analysis for $C_{14}H_{20}ClNO_4$ (301.78): calculated: C 55.72%, H 6.68%; found: C 55.72%, H 6.42%.

The following acid addition salts can be prepared in an analogous way:

1-[bis(hydroxymethyl)-methyl]-6,7-diethoxy-3,4-dihydroisoquinoline hydrochloride; melting point: 164° to 167 C.° (ethanol/ether).

Analysis for $C_{16}H_{24}ClNO_4$ (329.81): calculated: C 58.27%, H 7.33%, N 4.25%; found: C 58.60%, H 7.45%, N 4.76%; and 1-[bis(hydroxymethyl)-methyl]-6,7-dimethoxy-3,4-dihydroisoquinoline hydrobromide; melting point: 194° to 197 C.° (methanol/ether).

Analysis for $C_{14}H_{20}BrNO_4$ (346.23): calculated: C 48.57%, H 5.82%; found: C 48.52%, H 5.87%.

EXAMPLE 9

Preparation of
1-[bis(hydroxymethyl)-methyl]-6,7-dimethoxy-3,4-dihydroisoquinoline To 0.01 mole of 1-(β-hydroxyethyl)-6,7-dimethoxy-3,4-dihydroisoquinoline 2 ml of a 37% aqueous formaldehyde solution are added, and the mixture is boiled in 30 ml of methanol for 2 hours. After evaporation the obtained oily residue is triturated with ether. Crystallization of the obtained product from a mixture of acetone and ether affords the desired compound, which has the same spectral characteristics as the product of Example 1. Melting point: 129° to 131 C.°

EXAMPLE 10

Preparation of
1-[bis(hydroxymethyl)-methyl]-6,7-dimethoxy-1,2,3,4-tetrahydroisoquinoline To a solution of 0.1 mole (26.5 g) of 1-[bis(hydroxymethyl)-methyl]-6,7-dimethoxy-3,4-dihydroisoquinoline prepared according to Example 1 in 60 ml of methanol 0.4 mole (15.1 g) of sodium tetrahydroborate (III) are added under cooling with ice and stirring, taking care that the temperature of the reaction mixture should not exceed 10 C.° The reaction mixture is stirred for 5 hours and is then allowed to warm up to room temperature. The mixture and, respectively, the excess of sodium tetrahydroborate (III) is decomposed with an acid, and after alkalization the mixture is evaporated. The reaction mixture is then extracted with 100 ml of water and three 80 ml portions of chloroform. The organic phase is dried over sodium sulfate, evaporated, and the product obtained is recrystallized from a mixture of benzene and ether.

Melting point: 139° to 141 C.°

Analysis for $C_{14}H_{21}NO_4$ (267.33): calculated: C 62.90%, H 7.92%, N 5.24%; found: C 62.64%, H 8.06%, N 5.11%

The 6,7-diethoxy analogue of the above compound can be prepared in an analogous manner, starting from 1-[bis(hydroxymethyl)-methyl]-6,7-diethoxy-3,4-dihydroisoquinoline; melting point: 127° to 128 C.° (benzene).

Analysis for $C_{16}H_{25}NO_4$ (295.38): calculated: C 65.06%, H 8.53%, N 4.74%; found: C 64.75%, H 8.78%, N 4.38%.

EXAMPLE 11

Preparation of
1-[bis(hydroxymethyl)-methyl]-6,7-dihydroxy-3,4-dihydroisoquinoline hydrobromide 0.01 mole (2.65 g) of 1-[bis(hydroxymethyl)-methyl]-6,7-dimethoxy-3,4-dihydroisoquinoline is boiled with 10 ml of a 46% hydrogen bromide solution for 4 hours. The mixture is evaporated and the residue is triturated with acetone to yield the aimed compound.

Yield: 82%.

Melting point: 179° to 181 C.° (ethanol).

Analysis for $C_{12}H_{16}BrNO_4$ (318.17): calculated: C 45.29%, H 5.07%, N 4.40%; found: C 45.65%, H 5.25%, N 4.65%.

EXAMPLE 12

Preparation of
1-[bis(hydroxymethyl)-methyl]-6,7-dihydroxy-3,4-dihydroisoquinoline hydrobromide Following the procedure described in Example 11 but starting from 1-[bis(hydroxymethyl)-methyl]-6,7-diethoxy-3,4-dihydroisoquinoline, the aimed compound is obtained in a yield of 77%.

Melting point: 178° to 180 C.° /ethanol/.

The product, when admixed with the product obtained in Example 11, does not give any melting point depression.

EXAMPLE 13

Preparation of
1-[bis(hydroxymethyl)-methyl]-6,7-dimethoxy-1,2,3,4-tetrahydroisoquinoline 0.01 mole (2.65 g) of 1-[bis(hydroxymethyl)-methyl]-6,7-dimethoxy-3,4-dihydroisoquinoline is dissolved in 50 ml of ethanol, and the mixture is reduced in hydrogen atmosphere, in the presence of a 10% platinum-on-activated carbon catalyst, under normal conditions. After uptake of the calculated amount of hydrogen (1 to 2 hours), the catalyst is filtered off and the filtrate is evaporated to yield the aimed compound in crystalline form.

Yield: 95%.

Melting point: 140° to 141 C.° (benzene/ether).

The product obtained does not give any melting point depression when admixed with the product prepared according to Example 10.

EXAMPLE 14

Preparation of
1-[bis(hydroxymethyl)-methyl]-6,7-dimethoxy-1,2,3,4-tetrahydroisoquinoline Following the procedure described in Example 13 but using 0.01 g of a 10% palladium-on-charcoal catalyst, the aimed compound is obtained in a yield of 86%.

Reaction time: 4 to 6 hours.

Melting point: 139° to 141 C.° (benzene/ether).

The product obtained does not give any melting point depression when admixed with the products obtained in Examples 10 and 13.

EXAMPLE 15

Preparation of the acid addition salts of tetrahydrocompounds

The acid addition salts of the compounds prepared according to Example 10 are prepared as described in Example 8. The physical and analytical characteristics of the compounds obtained are as follows:

1-[bis(hydroxymethyl)-methyl]-6,7-dimethoxy-1,2,3,4-tetrahydroisoquinoline hydrochloride; melting point: 218° to 220 C.° (methanol/ether).

Analysis for $C_{14}H_{22}ClNO_4$ (303.84): calculated: C 55.35%, H 7.30%; found: C 54.96%, H 7.46%.

1-[bis(Hydroxymethyl)-methyl]-6,7-diethoxy-1,2,3,4-tetrahydroisoquinoline hydrochloride; melting point: 199° to 201 C.° (ethanol/ether).

Analysis for $C_{16}H_{26}ClNO_4$ (331.84): calculated: 57.91%, H 7.89%; found: 57.89%, H 8.33%.

1-[bis(Hydroxymethyl)-methyl]-6,7-dimethoxy-1,2,3,4-tetrahydroisoquinoline hydrobromide; melting point:
220° to 223 C.° (ethanol/ether).

Analysis for $C_{14}H_{22}BrNO_4$ (348.24): calculated: C 48.29%, H 6.37%; found: C 48.04%, H 6.46%.

1-[bis(Hydroxymethyl)-methyl]-6,7-diethoxy-1,2,3,4-tetrahydroisoquinoline hydrobromide; melting point: 185° to 187 C.° (ethanol).

Analysis for $C_{16}H_{26}BrNO_4$ (376.30): calculated: C 51.07%, H 6.96%, N 3.72%; found: C 51.03%, H 6.87%, N 3.94%.

REFERENCE EXAMPLE

Preparation of
1-[bis(hydroxymethyl)-methyl]-2-methyl-6,7-dimethoxy-1,2,3,4-tetrahydroisoquinoline hydrochloride To 0.0125 mole (3.33 g) of 1-[bis(hydroxymethyl)-methyl]-6,7-dimethoxy-1,2,3,4-tetrahydroisoquinoline 15 ml of a 37% aqueous formaldehyde solution and 15 ml of 99% formic acid are added, and the mixture is kept at 100 C.° for 10 hours. After cooling, 50 ml of a 15% aqueous hydrogen chloride solution is added to the reaction mixture, which is then evaporated under reduced pressure. The residue is thoroughly dehydrated and triturated with a small amount of acetone to yield the aimed compound with a melting point of 199° to 201 C.° (ethanol/ether).

Yield: 70%.

Analysis for $C_{15}H_{26}ClNO_4$ (317.81): calculated: C 56.68%, H 7.61%, N 4.41%; found: C 56.48%, H 7.43%, N 4.23%.

The product obtained has analgesic and antipyretic activity.

What is claimed is:

1. Compound of the formula (I)

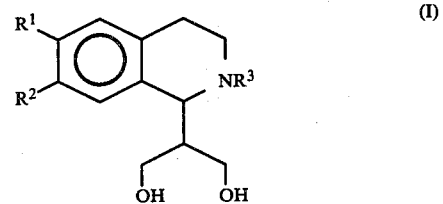

wherein
$R^1$ and $R^2$ represent hydroxyl or alkoxy having from 1 to 6 carbon atoms,
$R^3$ is hydrogen or a single electron pair,
and the dotted line represents an optional double bond,
and pharmaceutically acceptable salts thereof.

2. A compound selected from the group consisting of
1-[bis(hydroxymethyl)-methyl]-6,7-dimethoxy-3,4-dihydroisoquinoline and acid addition salts thereof,
1-[bis(hydroxymethyl)-methyl]-6,7-diethoxy-3,4-dihydroisoquinoline and acid addition salts thereof,
1-[bis(hydroxymethyl)-methyl]-6,7-dihydroxy-3,4-dihydroisoquinoline and acid addition salts thereof,
1-[bis(hydroxymethyl)-methyl]-6,7-dimethoxy-1,2,3,4-tetrahydroisoquinoline and acid addition salts thereof,
1-[bis(hydroxymethyl)-methyl]-6,7-diethoxy-1,2,3,4-tetrahydroisoquinoline and acid addition salts thereof.

3. A pharmaceutical composition having neuroleptic and anticonvulsive activities which comprises: an effective amount of at least one compound of the formula (I) of claim 1, or a pharmaceutically acceptable salt thereof, in admixture with conventional pharmaceutical carriers and/or diluents.

* * * * *